United States Patent [19]
Hughes

[11] Patent Number: 6,051,187
[45] Date of Patent: Apr. 18, 2000

[54] REUSABLE STEAM TEST PACK

[76] Inventor: Charles A. Hughes, 30 Boulder Creek Dr., Rush, N.Y. 14543

[21] Appl. No.: 09/050,634

[22] Filed: Mar. 30, 1998

[51] Int. Cl.[7] .............................. A61L 2/26; G01N 21/78
[52] U.S. Cl. ............................ 422/26; 422/56; 422/58; 422/61; 206/439; 435/31
[58] Field of Search .............................. 422/26, 300, 295, 422/58, 61, 56; 206/439; 435/287.4, 31

[56] References Cited

U.S. PATENT DOCUMENTS

| | | |
|---|---|---|
| 4,121,714 | 10/1978 | Daly et al. . |
| 4,636,472 | 1/1987 | Bruso . |
| 4,692,307 | 9/1987 | Bruso . |
| 4,828,797 | 5/1989 | Zwarun et al. . |
| 4,902,478 | 2/1990 | Hambleton . |
| 4,918,003 | 4/1990 | Macaro et al. . |
| 5,066,464 | 11/1991 | Augurt . |
| 5,200,147 | 4/1993 | Augurt . |
| 5,204,062 | 4/1993 | Buglino et al. . |
| 5,217,901 | 6/1993 | Dyckman . |

Primary Examiner—Robert J. Warden, Sr.
Assistant Examiner—Jennifer C. McNeil
Attorney, Agent, or Firm—Wall Marjama Bilinski & Burr

[57] ABSTRACT

A reusable test pack suitable for monitoring a steam sterilization process which includes an outer sealable pouch which is permeable to steam. A removable insert is contained within said pouch, and contains a chamber for holding a sterilization indicator device. A sterilization indicator device is contained within the chamber and a data card is contained within the pouch, and positioned to cover the indicator device.

32 Claims, 4 Drawing Sheets

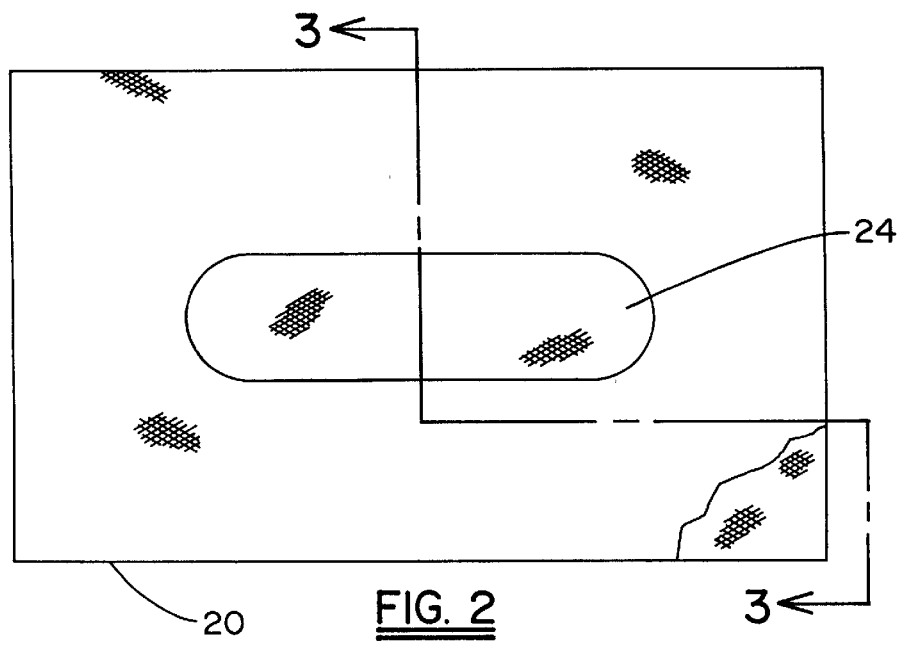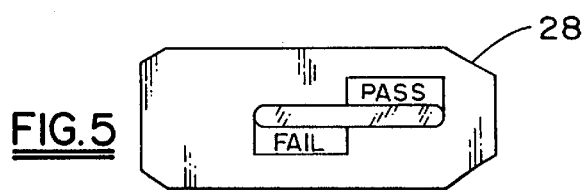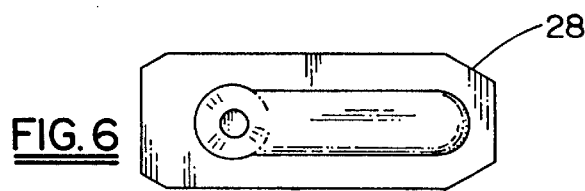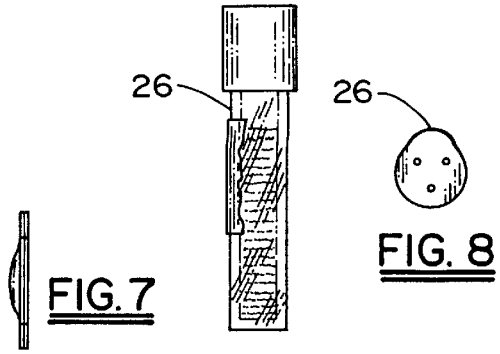

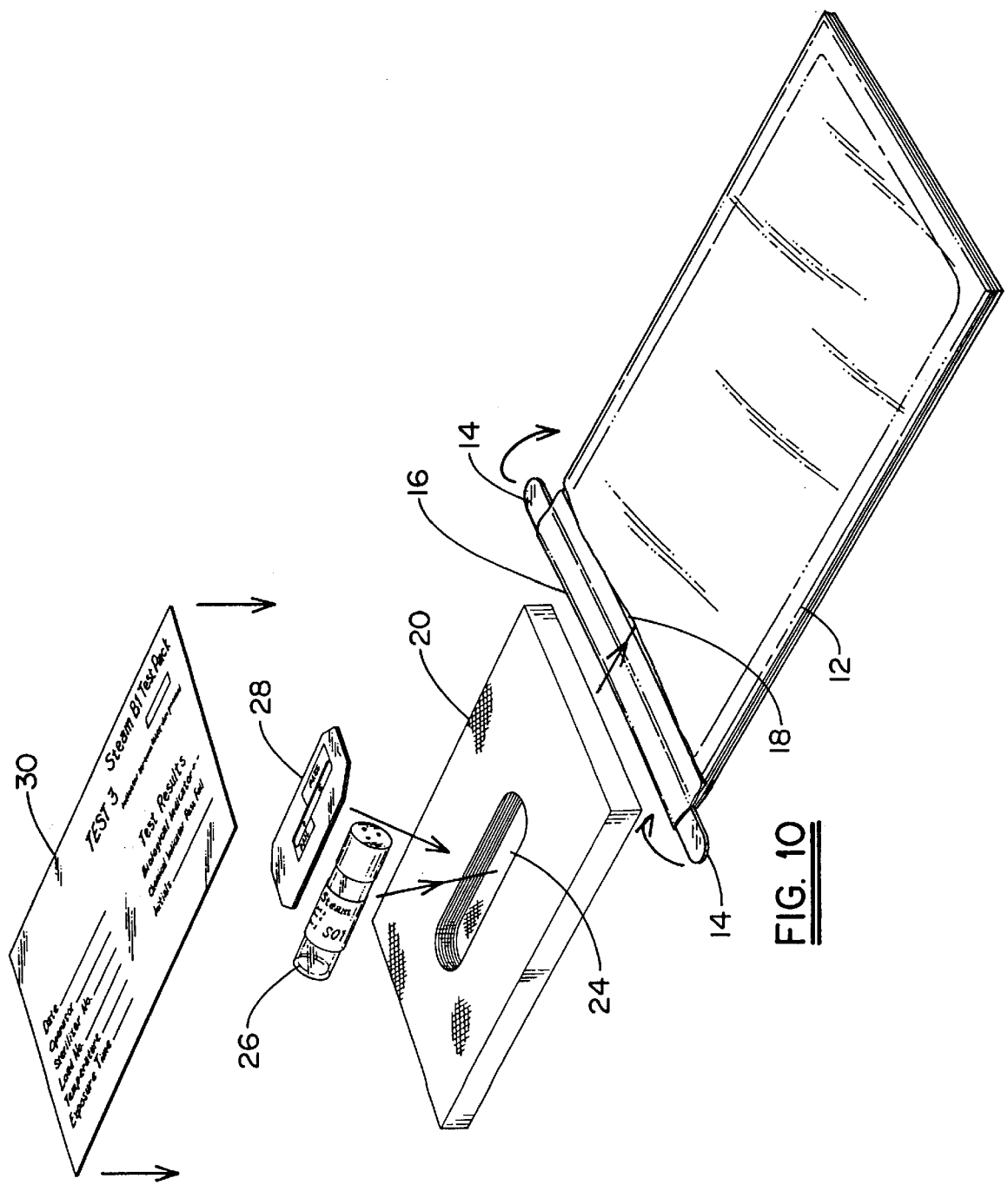

(x2)

REUSABLE STEAM TEST PACK

FIELD OF THE INVENTION

This invention relates generally to a device for monitoring steam sterilization, and more specifically to a reusable steam test pack.

BACKGROUND OF THE INVENTION

In the field relating to monitoring steam sterilization, the standard in the industry is a single-use disposable device. The following prior art typifies the state of the art with respect to sterilization test devices that are currently available.

U.S. Pat. No. 4,636,472 teaches a disposable sterilization test pack in which a biological indicator is contained or sandwiched within a cavity surrounded by porous pads which are surrounded by an outer paper wrapping.

U.S. Pat. No. 5,217,901 teaches a sterilization biological test pack in which a biological indicator is surrounded by a series of planar paper sheets. This configuration is surrounded by an outer wrap which would render the device unsuitable for use as a reusable device.

U.S. Pat. No. 4,918,003 discloses a biological test device for steam sterilization in which the device is described as being a disposable package. It is similar in structure and function to the device taught by the above-mentioned '472 patent.

U.S. Pat. Nos. 4,692,037; 4,902,478 and 5,204,062 all teach test packs for indicator devices which utilize a test sheet as an indicator.

U.S. Pat. No. 5,066,464 teaches a pre-vacuumed steam sterilization test pack which has a triangular truncated shape and an internal indicator strip.

None of the devices described above, which are typical of the state of the art, teach a device which may be reused a plurality of times. Furthermore, the devices described above because of their single use, are relative expensive to use because of their disposable nature and present problems with regard to storage.

It is therefore an objective of the present invention to provide a reusable test pack for monitoring steam sterilization which can be reused a plurality of times without any loss or degradation in performance.

It is a further object of the present invention to provide an economical compact reusable biological test pack which provides for high performance and reduces storage problems.

It is a further object of the present invention to provide for a reusable biological monitoring test pack which has the option of utilizing both biological and/or chemical integrators.

SUMMARY OF THE INVENTION

The present invention is directed to a reusable test pack suitable for monitoring sterilization processes. The device comprises a reusable outer containment pouch preferably made of a porous or steam permeable plastic material. The pouch contains a removable insert portion which comprises a breathable textile fabric containing an internal chamber which is adapted to store a biological indicator and/or chemical integrator. The device is further adapted to receive an additional insert in the form of a paper load card which is placed over the internal chamber. The containment pouch is then sealed and exposed to the sterilization cycle. The device of the present invention complies with all AAMI recommendations for pre-vacuum and gravity porous load steam sterilization testing.

The present invention provides equivalent performance to the AAMI described Towel Pack comprising of 16 freshly laundered folded Huckaback cotton towels. Each towel is approximately 16"×26" and is folded so that when the towels are laid upon each other the stack is 9"×9"×6" high and sealed with autoclave tape.

BRIEF DESCRIPTION OF THE DRAWING

For a fuller understanding of the nature and objects of the invention, reference should be made to the following detailed description of a preferred mode of practicing the invention, read in connection with the accompanying drawings, in which:

FIG. 2 is a top view of the insert.

FIG. 3 is a cross-sectional view along lines 3—3 of FIG. 2.

FIG. 4 is a top view of the load card.

FIG. 5 is a top view of a prior art chemical indicator.

FIG. 6 is a bottom view of the device of FIG. 5.

FIG. 7 is an end view of the device of FIG. 6.

FIG. 8 is a top view of the device of FIG. 9.

FIG. 9 is a side view of a prior art biological indicator.

FIG. 10 is an exploded view of the device of the present invention.

DETAILED DESCRIPTION OF THE INVENTION

Figure 1:
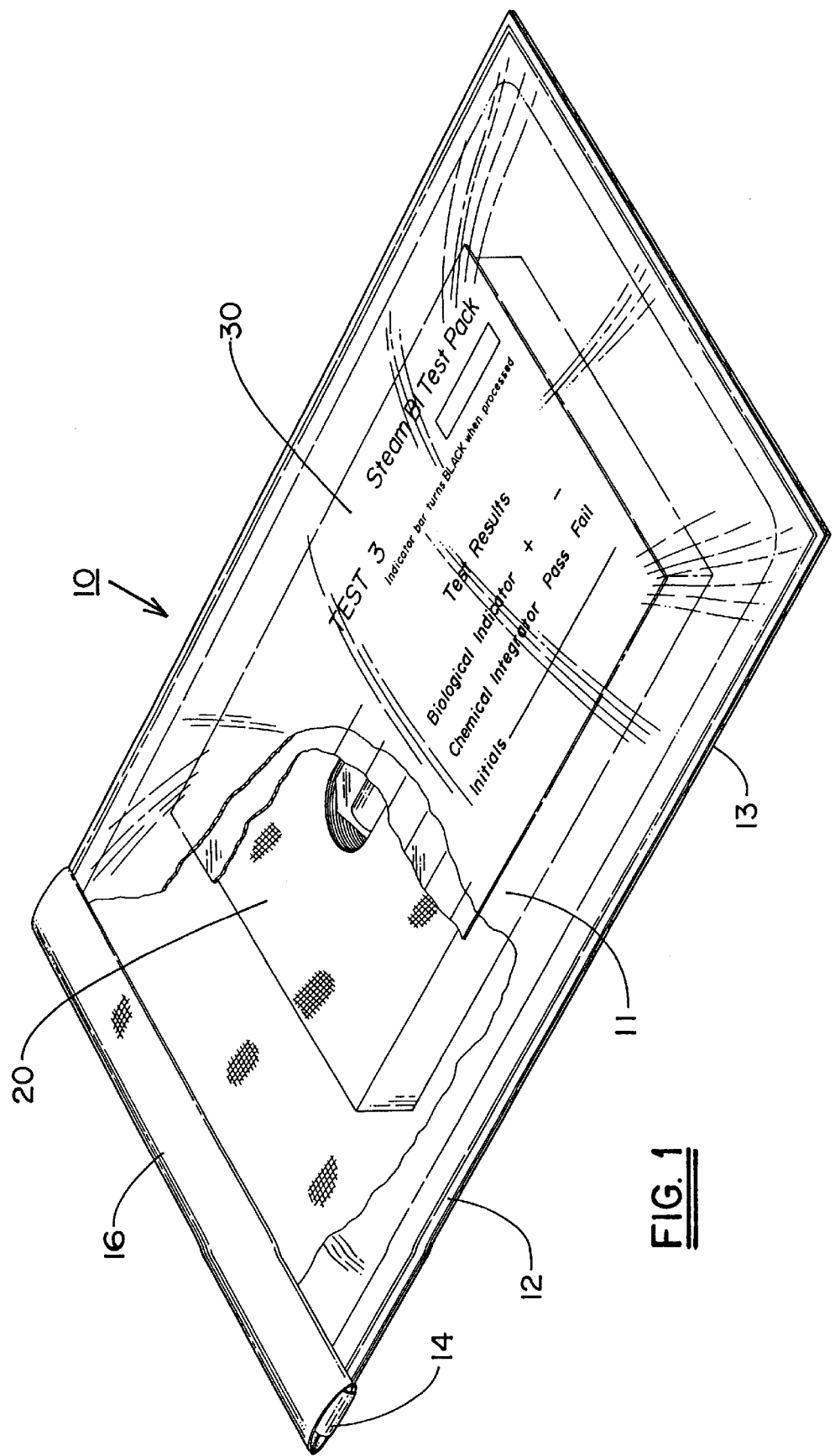
FIG. 1 is a partial perspective view of the device of the present invention.

With reference to FIG. 1, reference character 10 depicts a perspective view of the reusable sterilization test pack of the present invention. The test pack comprises a breathable textile-plastic outer containment pouch 12 having a transparent plastic top surface 11 and an opaque bottom surface 13. Pouch 12 further contains closure means 14 and 16 at one end which enable the device to seal opening 18 (FIG. 10) when the device is ready for use. A reusable test pack insert 20 of breathable textile fabric, which contains an inner chamber or well 24, is placed within the outer pouch when the device is in use. The insert typically comprises a ½ inch thick stack of three by five inch breathable textile fabric 22. The chamber or well 24 contained within insert 20 contains either a conventional single chemical integrator or a self-contained single biological indicator, or in certain applications, one of each indicators. A single, three by five inch, porous paper loading card 30 is placed in the chamber and lovers the chemical and/or biological indicators during use.

FIG. 10 illustrates an exploded perspective view of the device of the present invention with FIG. 1 illustrating all of the components which will be placed within the sealed pouch 12. The individual components, including the test pack load card and chemical and biological indicators 28 and 26 respectively, are illustrated more clearly in FIGS. 2–9.

In operation, a load record card 30 is selected for use and the appropriate sterilizer information is recorded on the card. With each kit, the cards are consecutively numbered from 1 through 25 for inventory control, with 25 sterilization cycles or uses being the lifetime of the kit, including the outer containment pouch and insert.

A biological and/or chemical indicator are selected from their respective storage box and placed inside chamber 24 as illustrated in FIGS. 1 and 10. The load record card 30 is then placed on top of the test pack insert 20 face up so that the card can be seen as illustrated in FIGS. 1 and 10. The load record card and/or it's position within the pouch, can lengthen or control the response time of the biological indicator and/or chemical indicator. The outer sterilization pouch 12 is sealed by folding over the end 16 and bending over metal tabs 14 as illustrated in FIGS. 1 and 10. Typically, the end is folded over three times and with the metal tabs then being bent inward.

Figures 11, 12:
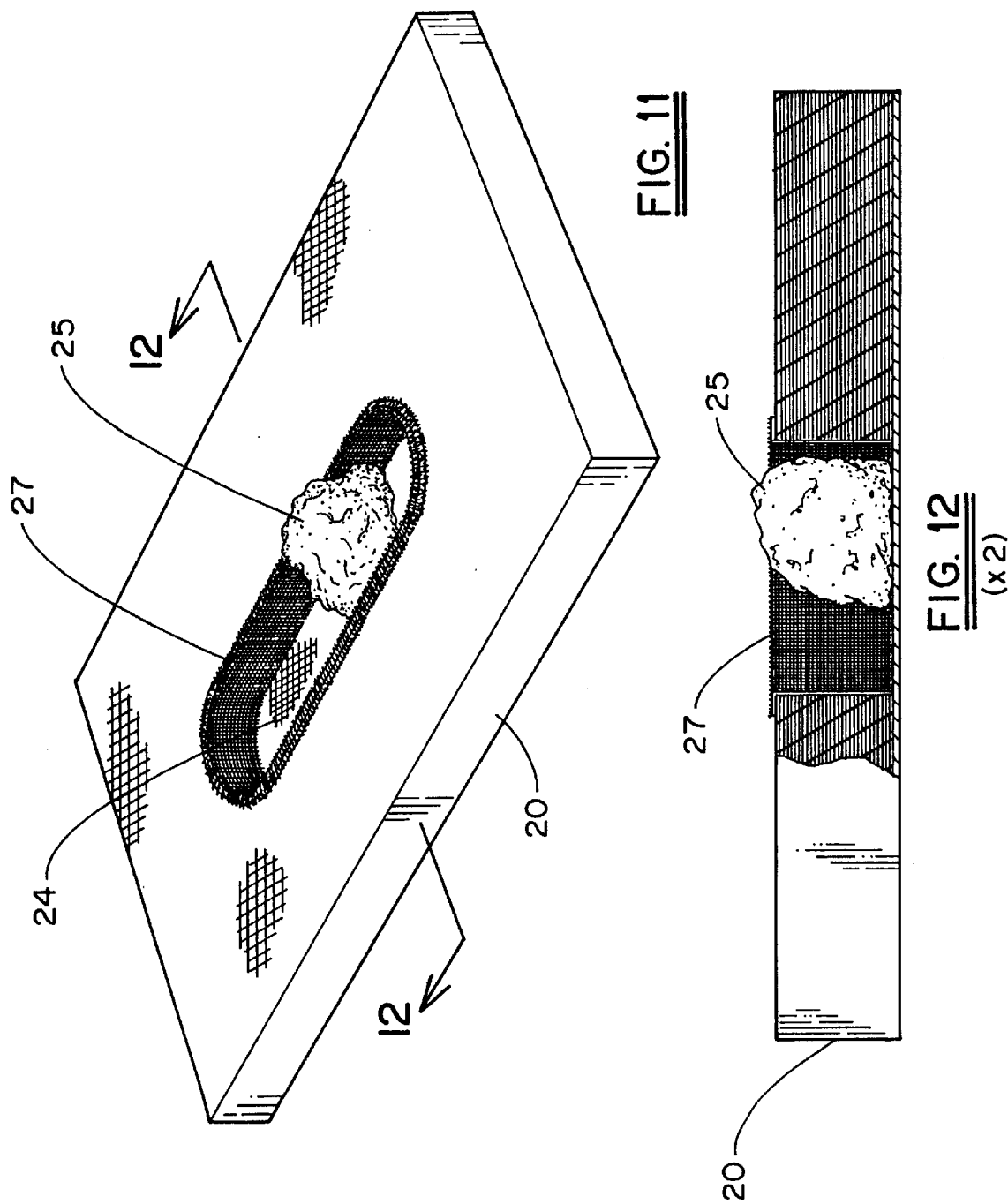
FIG. 11 is a perspective view of the insert used in the present invention which contains absorbent material.
FIG. 12 Ls a sectional view of the insert of FIG. 11 taken along line 12—12.

In another embodiment, the response time of the biological indicator and/or chemical indicator can be lengthen or controlled by the addition of an absorbent material in the pouch. For example the absorbent material 25 can be loosely contained inside chamber 24 or formed as a lining 27 around the inside wall of the chamber as shown in FIG. 11 and 12. Any suitable absorbent material can be used. Typical materials include: natural and synthetic sponges, gauze, cotton and foam.

Carrying out conventional AAMI guidelines, the test pack is then placed face up in a fully loaded sterilization chamber on the bottom shelf near the drain and a normal sterilization cycle is run as specified by the sterilizer manufacturer.

Upon completion of the sterilization cycle, the test pack is removed from the sterilizer and allowed to cool for ten minutes. The test pack is then opened and the load control card integrator checked for proper processing. When using a biological indicator, it is activated prior to placement in a 55–60° C. incubator.

When using the biological indicator, it is incubated with an unprocessed control biological indicator for 48 hours. Biological indicators which are positive (that is non-sterile) will change color from purple to yellow during incubation. All results are recorded on the load record card.

The test pack of the present invention provides an advantage over the prior art in that the device is a reusable product that can be reused up to 25 times without loss of performance. The test pack is contained in a reusable containment pouch whereas other products of the prior art are normally contained in cardboard boxes or a single use wrap. The insert portion of the device, which is also reusable, is a breathable textile (preferably polypropylene) fabric with a notched chamber or well capable of storing a biological indicator, a chemical integrator or both. The device of the present invention complies with AAMI recommendations for pre-vacuum and gravity porous load steam sterilizer testing, and is made in a convenient relatively small size, i.e. 5 in.×9 in. containment pouch which allows for convenient storage using minimal space.

A biological indicator suitable for use in the present invention is one sold under the trademark SporView available from SPS Medical of Rush, New York. A suitable chemical indicator which may be used with the device of the present invention is sold under the trademark ChemView and is also available from SPS Medical.

The data load card may be made of any suitable paper which will effectively cover the chamber and keep its integrity during the sterilization cycle. A suitable material comprises paper tag stock, paperboard or other suitable biodegradeable material.

The outer containment pouch and insert may be made of any porous or breathable textile fabric or plastic. A suitable material comprises polypropylene. A preferred material comprises spunbound polypropylene available from Lantor Ltd. of Manchester, England. The transparent top surface of the pouch in one embodiment is made of a propylene co-polymer resin available from HIMONT Canada, Inc. of Montreal, Canada under the trademark Pro-fax®.

While the present invention has been particularly shown and described with reference to the preferred mode as illustrated in the drawings, it will be understood by one skilled in the art that various changes in detail may be effected therein without departing from the spirit and scope of the invention as defined by the claims.

I claim:

1. A reusable test pack suitable for monitoring a steam sterilization process which comprises:
    (a) an outer sealable pouch which is permeable to steam and which is made of a durable reusable material;
    (b) a removable insert which is made of a durable reusable material contained within said pouch, said insert containing means for holding a sterilization indicator device;
    (c) at least one sterilization indicator device contained within said holding means; and
    (d) a data card contained within said pouch and positioned to cover said indicator device thereby forming an outer layer over said means for holding said indicator device, said outer layer being capable of controlling the response time of said indicator device to the sterilization cycle and wherein said outer pouch and said insert can be used for up to twenty five sterilization cycles.

2. The device of claim 1 in which the indicator device is a biological indicator.

3. The device of claim 1 in which the indicator device is a chemical indicator.

4. The device of claim 1 in which the outer pouch is made of a plastic material.

5. The device of claim 1 in which the outer pouch comprises a breathable textile material.

6. The device of claim 1 in which the outer pouch is made of polypropylene.

7. The device of claim 1, which further includes an absorbent material contained within said pouch.

8. A reusable test pack suitable for monitoring a steam sterilization process which comprises:
    (a) an outer sealable plastic pouch which is permeable to steam and which is made of a durable reusable material;
    (b) a removable insert which is made of a durable reusable material contained within said pouch, said insert containing an internal chamber for holding a sterilization indicator device;

(c) a biological indicator device contained within said holding means; and (d) a paper data card contained within said pouch, and positioned to cover said indicator device thereby forming an outer layer over said means for holding said indicator device, said outer layer being capable of controlling the response time of said indicator device to the sterilization cycle and wherein said outer pouch and said insert can be used for up to twenty five sterilization cycles.

9. The device of claim 8 in which the outer pouch is made of a plastic material.

10. The device of claim 8 in which the outer pouch comprises a breathable textile material.

11. The device of claim 8 in which the outer pouch is made of polypropylene.

12. A reusable test pack suitable for monitoring a steam sterilization process which comprises:

(a) an outer sealable plastic pouch which is permeable to steam and which is made of a durable reusable material;

(b) a removable insert which is made of a durable reusable material contained within said pouch, said insert containing an internal chamber for holding a sterilization indicator device;

(c) a chemical indicator device contained within said holding means; and (d) a paper data card contained within said pouch, and positioned to cover said indicator device thereby forming an outer layer over said means for holding said indicator device, said outer layer being capable of controlling the response time of said indicator device to the sterilization cycle and wherein said outer pouch and said insert can be used for un to twenty five sterilization cycles.

13. The device of claim 12 in which the outer pouch is made of a plastic material.

14. The device of claim 12 in which the outer pouch comprises a breathable textile material.

15. The device of claim 12 in which the outer pouch is made of polypropylene.

16. A reusable test pack suitable for monitoring a steam sterilization process which comprises:

(a) an outer sealable plastic pouch which is permeable to steam and which is made of a durable reusable material;

(b) a removable insert which is made of a durable reusable material contained within said pouch, said insert containing an internal chamber for holding a sterilization indicator device;

(c) at least one sterilization indicator device contained within said holding means; and (d) a paper data card contained within said pouch, and positioned to cover said indicator device thereby forming an outer layer over said means for holding said indicator device, said outer layer being capable of controlling the response time of said indicator device to the sterilization cycle and wherein said outer touch and said insert can be used for up to twenty five sterilization cycles.

17. The device of claim 16 in which the outer pouch is made of a plastic material.

18. The device of claim 16 in which the outer pouch comprises a breathable textile material.

19. The device of claim 16 in which the outer pouch is made of polypropylene.

20. A reusable test pack suitable for monitoring a steam sterilization process which comprises:

(a) an outer sealable plastic pouch which is permeable to steam and which is made of a durable reusable material;

(b) a removable insert which is made of a durable reusable material contained within said pouch, said insert containing an internal chamber for holding a sterilization indicator device;

(c) a biological and chemical sterilization indicator device contained within said internal chamber; and (d) a paper data card contained within said pouch, and positioned to cover said indicator device thereby forming an outer layer over said means for holding said indicator device, said outer layer being capable of controlling the response time of said indicator device to the sterilization cycle and wherein said outer pouch and said insert can be used for up to twenty five sterilization cycles.

21. The device of claim 20 in which the outer pouch is made of a plastic material.

22. The device of claim 20 in which the outer pouch comprises a breathable textile material.

23. The device of claim 20 in which the outer pouch is made of polypropylene.

24. A method for monitoring a steam sterilization process which comprises:

(a) providing a durable reusable pack which includes an outer sealed pouch which is permeable to steam, a removable insert which is contained within said pouch, said insert containing means for holding a sterilization indicator device, at least one sterilization indicator device contained within said holding means, and a data card contained within said pouch, and positioned to cover said indicator device thereby forming an outer layer over said means for holding said indicator device, said outer layer being capable of controlling the response time of aid indicator device to the sterilization cycle and wherein said outer pouch and said insert can be used for up to twenty five sterilization cycles, (b) subjecting said pouch to a sterilization cycle, (c) processing and/or evaluating said indicator device to confirm sterilization parameters, and (d) repeating steps (b) and (c) with the test pack of (a) using a new data card and sterilization indicator device.

25. The method of claim 24 in which the test pack outer pouch and removable insert are used for up to 25 sterilization cycles.

26. The method of claim 24 in which the indicator device is a biological indicator.

27. The method of claim 24 in which the indicator device is a chemical indicator.

28. The method of claim 24 in which the outer pouch is made of a steam permeable plastic; material.

29. The method of claim 24 in which the outer pouch comprises a breathable textile material.

30. The method of claim 24 in which the outer pouch and insert are made of polypropylene.

31. Method for monitoring a steam sterilization process which comprises:

(a) providing a durable reusable pack which includes an outer sealed polypropylene pouch which is permeable to steam, a removable polypropylene insert which is contained within said pouch, said insert containing an open internal chamber for holding a sterilization indicator device, at least one sterilization indicator device contained within said chamber, and a paper data card contained within said pouch, and positioned to cover said indicator device thereby forming an outer layer over said means for holding said indicator device, said outer layer being capable of controlling the response time of said indicator device to the sterilization cycle and wherein said outer pouch and said insert can be used for up to twenty five sterilization cycles, (b) subjecting said pouch to a sterilization cycle, (c) processing and/or evaluating said indicator device to confirm sterilization parameters, and (d) repeating steps (b) and (c) with the test pack of (a) using a new data card and sterilization indicator device.

32. The method of claim 31 in which the test pack outer pouch and removable insert are used for up to 25 sterilization cycles.

* * * * *